US012793870B2

(12) United States Patent
Heibel et al.

(10) Patent No.: US 12,793,870 B2
(45) Date of Patent: Nov. 10, 2026

(54) DEVICES, SYSTEMS, AND METHODS FOR DELIVERING DELTA RADIATION USING PROMPT NEUTRON CAPTURE GAMMA RADIATION

(71) Applicant: Westinghouse Electric Company LLC, Cranberry Township, PA (US)

(72) Inventors: Michael D. Heibel, Broomfield, CO (US); Devon Gerstein, Wayne, PA (US); Maureen Gilthii, Landsdowne, PA (US); Yazhu Jiang, Stage College, PA (US); Jack Decker, Stage College, PA (US); Emerie Stagner, Saylorsburg, PA (US); Jeremy Dunston, South Orange, NJ (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 514 days.

(21) Appl. No.: 18/547,952

(22) PCT Filed: Feb. 23, 2022

(86) PCT No.: PCT/US2022/070785
§ 371 (c)(1),
(2) Date: Aug. 25, 2023

(87) PCT Pub. No.: WO2022/183181
PCT Pub. Date: Sep. 1, 2022

(65) Prior Publication Data

US 2024/0136085 A1 Apr. 25, 2024
US 2024/0233976 A9 Jul. 11, 2024

Related U.S. Application Data

(60) Provisional application No. 63/153,494, filed on Feb. 25, 2021.

(51) Int. Cl.
*A61N 5/10* (2006.01)
*G21K 1/02* (2006.01)
(Continued)

(52) U.S. Cl.
CPC ................ *G21K 5/02* (2013.01); *A61N 5/10* (2013.01); *A61N 5/1077* (2013.01); *G21K 1/02* (2013.01);
(Continued)

(58) Field of Classification Search
None
See application file for complete search history.

(56) References Cited

U.S. PATENT DOCUMENTS 10,441,815 B2 10/2019 Akabori et al.
10,456,469 B2 10/2019 Serrano-Ojeda
(Continued)

FOREIGN PATENT DOCUMENTS

JP 2007242422 A 9/2007
JP 2018529765 A 10/2018
(Continued)

OTHER PUBLICATIONS

International Search Report and Written Opinion for corresponding International PCT Application No. PCT/US2022/070785, dated Aug. 17, 2022.

*Primary Examiner* — Eliza W Osenbaugh-Stewart
(74) *Attorney, Agent, or Firm* — K&L Gates LLP

(57) ABSTRACT

Devices, systems, and methods for delivering delta radiation using prompt neutron capture gamma radiation are disclosed herein. In one aspect, a device for delivering delta radiation can include a neutron generator, an electron emitter, and an irradiation target. The neutron generator may be configured to generate a neutron flux field. The an irradiation target can include an irradiation target material having a high thermal
(Continued)

neutron cross section and can be configured to emit gamma radiation in response to exposure to the neutron flux field. The electron emitter can be configured to emit delta radiation in response to exposure to the gamma radiation. In some aspects, the irradiation target and the electron emitter can be configured to be positioned between the neutron generator and a surface of an object to deliver the delta radiation to a target region within the object.

20 Claims, 2 Drawing Sheets

(51) Int. Cl.

| | |
|---|---|
| ***G21K 1/10*** | (2006.01) |
| ***G21K 5/02*** | (2006.01) |
| ***G21K 5/04*** | (2006.01) |

(52) U.S. Cl.
CPC ................ *G21K 1/10* (2013.01); *G21K 5/04* (2013.01); *A61N 2005/1089* (2013.01); *A61N 2005/1094* (2013.01); *A61N 2005/1095* (2013.01)

(56) References Cited

U.S. PATENT DOCUMENTS

| | | | |
|---|---|---|---|
| 11,324,967 | B2 | 5/2022 | Heibel |
| 2012/0080618 | A1 | 4/2012 | Clayton et al. |

FOREIGN PATENT DOCUMENTS

| | | | |
|---|---|---|---|
| JP | 2018166716 | A | 11/2018 |
| JP | 2019080728 | A | 5/2019 |
| JP | 20210513893 | A | 6/2021 |
| KR | 101676963 | B1 | 11/2016 |
| WO | 2019160931 | A1 | 8/2019 |
| WO | 2022183181 | A1 | 9/2022 |

DEVICES, SYSTEMS, AND METHODS FOR DELIVERING DELTA RADIATION USING PROMPT NEUTRON CAPTURE GAMMA RADIATION

CROSS-REFERENCE TO RELATED APPLICATIONS

This application is a U.S. National Stage Entry under 35 U.S.C. § 371 of International Patent Application No. PCT/US2022/070785, entitled DEVICES, SYSTEMS, AND METHODS FOR DELIVERING DELTA RADIATION USING PROMPT NEUTRON CAPTURE GAMMA RADIATION, filed Feb. 23, 2022, which claims the benefit of and priority under 35 U.S.C. § 119(e) to U.S. Provisional Application No. 63/153,494 titled A METHOD AND DEVICE TO DELIVER DELTA-RADIATION USING PROMPT NEUTRON CAPTURE GAMMA RADIATION GENERATED DELTA-RADIATION, filed Feb. 25, 2021, the entire disclosures of which are hereby incorporated by reference in their entireties.

FIELD

The present disclosure is generally to related to devices, systems, and methods for delivering delta-radiation using prompt neutron capture gamma radiation. In some aspects, the devices, systems, and methods disclosed herein relate to delivering delta-radiation using prompt neutron capture gamma radiation to treat cancer or increase charge carrier concentration in a semiconductor material.

SUMMARY

The following summary is provided to facilitate an understanding of some of the innovative features unique to the aspects disclosed herein, and is not intended to be a full description. A full appreciation of the various aspects can be gained by taking the entire specification, claims, and abstract as a whole.

In various aspects, a device for delivering delta radiation using prompt neutron capture gamma radiation is disclosed herein. In one aspect, the device includes a neutron generator configured to generate a neutron flux field; an irradiation target configured to emit gamma radiation in response to exposure to the neutron flux field; and an electron emitter configured to emit delta radiation in response to exposure to the gamma radiation. The irradiation target and the electron emitter may be configured to be positioned between the neutron generator and a surface of an object to deliver the delta radiation to a target region within the object. The irradiation target may include an irradiation target material having a high thermal neutron cross section.

In various aspects, a method for delivering delta radiation using prompt neutron capture gamma radiation is disclosed herein. In one aspect, the method includes generating, by a neutron generator, a neutron flux field; emitting, by an irradiation target, gamma radiation in response to exposure to the neutron flux field; emitting, by an electron emitter, delta radiation in response to exposure to the gamma radiation; positioning the irradiation target and the electron emitter between the neutron generator and a surface of an object; and delivering the delta radiation to a target region within the object. The irradiation target can include an irradiation target material having a high thermal neutron cross section.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of any of the aspects disclosed herein.

BRIEF DESCRIPTION OF THE DRAWINGS

The various aspects described herein, together with objects and advantages thereof, may best be understood by reference to the following description, taken in conjunction with the accompanying drawings as follows.

Figure 1:
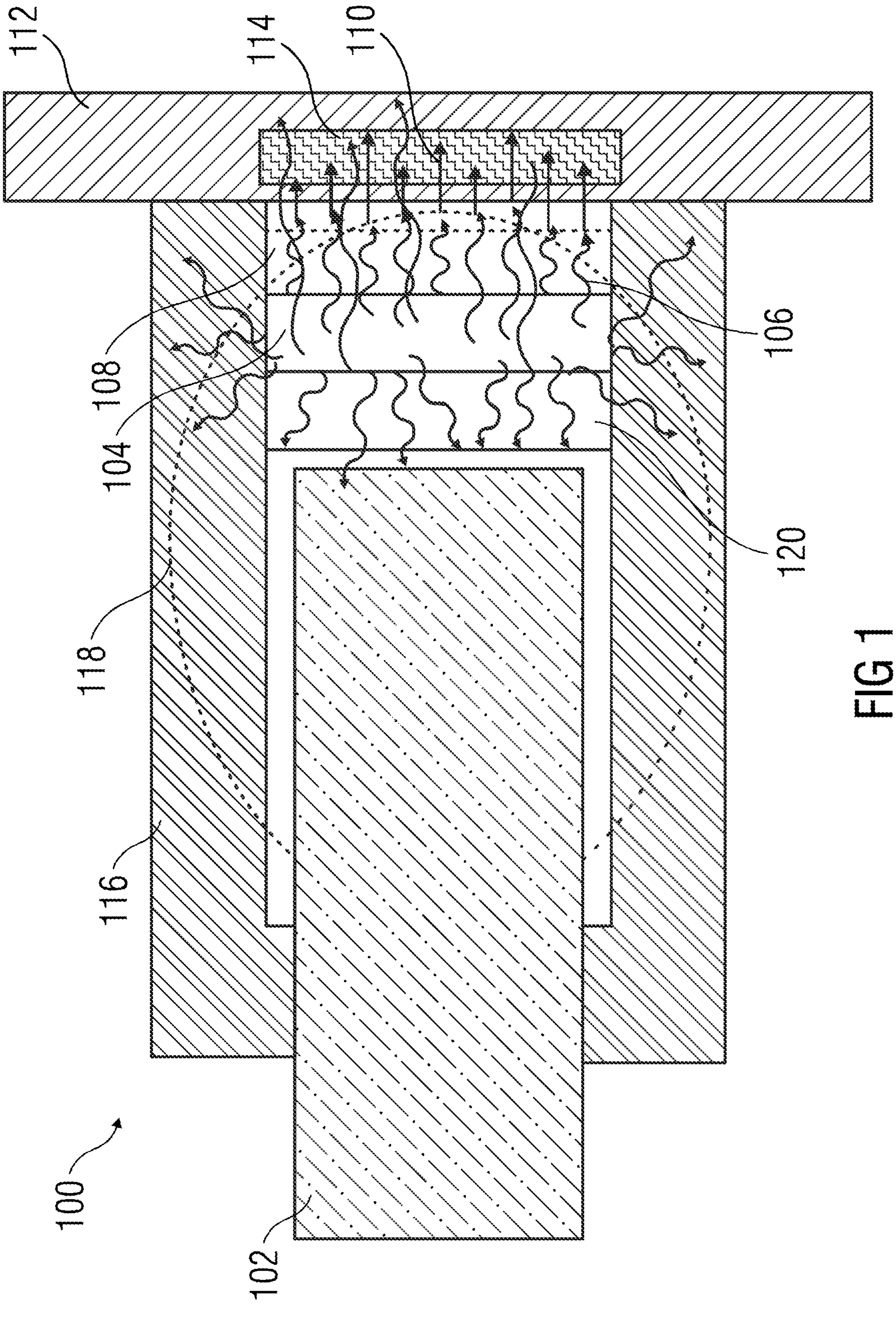
FIG. 1 is a cross-sectional schematic representation of a device for generating delta radiation using prompt neutron capture gamma radiation, in accordance with at least one non-limiting aspect of the present disclosure.

Corresponding reference characters indicate corresponding parts throughout the several views. The exemplifications set out herein illustrate various aspects of the present disclosure, in one form, and such exemplifications are not to be construed as limiting the scope of any of the aspects disclosed herein.

DETAILED DESCRIPTION

Numerous specific details are set forth to provide a thorough understanding of the overall structure, function, manufacture, and use of the aspects as described in the disclosure and illustrated in the accompanying drawings. Well-known operations, components, and elements have not been described in detail so as not to obscure the aspects described in the specification. The reader will understand that the aspects described and illustrated herein are non-limiting examples, and thus it can be appreciated that the specific structural and functional details disclosed herein may be representative and illustrative. Variations and changes thereto may be made without departing from the scope of the claims.

In the following description, like reference characters designate like or corresponding parts throughout the several views of the drawings. Also in the following description, it is to be understood that such terms as "forward," "rearward," "left," "right," "above," "below," "upwardly," "downwardly," and the like are words of convenience and are not to be construed as limiting terms.

According to the Skin Cancer Foundation, skin cancer is the most common cancer both in the United States and worldwide. One out of five Americans will develop skin cancer by the age of 70 and more than two people die of skin cancer in the United States every hour. For more details related to the prevalence of skin cancer and its causes, see Skin Cancer Facts and Statistics, Skin Cancer Foundation (Updated January 2022), https://www.skincancer.org/skin-cancer-information/skin-cancer-facts/, which is incorporated by reference herein in its entirety.

The treatment of highly localized carcinoma cells (e.g., tumors and cancers such as skin cancer) using ionizing radiation has proven to be relatively effective. However, the delivery of ionizing radiation to the body typically requires that the ionizing radiation pass through healthy tissue surrounding the intended target site. As a result, the healthy tissue may be damaged. Moreover, the concern for damage to health tissue limits the amount of ionization radiation that can be applied in a single treatment. Accordingly, multiple ionizing radiation treatments may be required which can result in accumulating tissue damage to healthy tissue and increased financial costs to the patient. Yet further, if the tumor or cancer cell growth rate outpaces the rate at which radiation treatments can be delivered to the patient, then the patient may ultimately succumb to the disease. Accordingly, new devices, systems, and methods of treatment that attack cancerous tissue with minimal effect on surrounding healthy tissue are needed.

In some aspects, Boron Neutron Capture Therapy (BNCT) can be used as an alterative to ionization radiation treatment BNCT can include implanting a therapeutic source including, for example, boron-10, proximate to carcinoma cells within the body of a patient. The therapeutic source may be irradiated with a neutron field generated outside of the body of the patient to generate alpha radiation and/or beta radiation. In some aspects, the therapeutic source can include electron emitter that generates delta radiation as a result of the emitted alpha radiation. Thus, the radiation generated using the therapeutic source and incident thermal neutrons can be used to kill the carcinoma cells. Additional details of some related aspects of this method are provided in U.S. patent application Ser. No. 16/102,063, titled SURGICALLY POSITIONED NEUTRON FLUX ACTIVATED HIGH ENERGY THERAPEUTIC CHARGED PARTICLE GENERATION SYSTEM, filed Aug. 8, 2018, now issued as U.S. Pat. No. 10,603,510, which is incorporated by reference herein in its entirety.

In some aspects, prompt neutron capture gamma radiation emitted by hafnium-174 (Hf-174) can be used to generate delta radiation as an alternative to ionization radiation treatment. This prompt neutron capture gamma radiation-based treatment method can include implanting a therapeutic source including Hafnium-174 proximate to carcinoma cells within the body of a patient. The therapeutic source may also include an electron emitter, such as, for example gold, platinum, tungsten, lead, or a combination thereof, at least partially surrounding the hafnium-174. The therapeutic source may be irradiated with a neutron field generated outside the body of the patient causing the hafnium-174 to emit gamma radiation. The gamma radiation emitted by the hafnium-174 can cause the electron emitter to emit delta radiation through Compton and photoelectric scattering interactions. Thus, the radiation generated using the therapeutic source and incident thermal neutrons can be used to kill the carcinoma cells. Additional details of some related aspects of this method are provided in U.S. patent application Ser. No. 16/274,808, titled THERAPEUTIC ELECTRON RADIATOR FOR CANCER TREATMENT, filed Feb. 13, 2019, which is incorporated by reference herein in its entirety.

However, there exists an opportunity to develop additional and/or improved alternatives to ionization radiation treatments. For example, prolonged exposure to gamma radiation emitted by hafnium-174 can be dangerous to the patient. Therefore, aspects of the methods described above may involve delivering a large neutron dose towards the patient in order to quickly generate enough gamma radiation to produce a therapeutic dose of delta radiation. Nevertheless, delta radiation generated using gamma radiation can exhibit a higher relative linear energy transfer rate and more sharply defined maximum penetration range into tissue compared to gamma radiation alone. Therefore, delta radiation generated using gamma radiation may be used to efficiently deliver radiation to cancerous tissue. In various aspects, the present disclosure provides devices, systems, and methods for delivering delta radiation to a target within an object, such as cancerous tissue within a patient, while also limiting the object's (e.g., patient's) exposure to thermal neutrons and gamma radiation.

FIG. 1 is a schematic representation of a device 100 for generating delta radiation 110 using prompt neutron capture gamma radiation 106, in accordance with at least one non-limiting aspect of the present disclosure. The device 100 includes a neutron generator 102 configured to generate thermal neutrons. In some aspects, the neutron 102 generator can be a commercially available, tubular-shaped electronic neutron generator. The thermal neutrons generated by the neutron generator 102 create a neutron flux field 118.

The device 100 further includes an irradiation target 104. The thermal neutrons (i.e., neutron flux field 118) generated by the neutron generator 102 may be directed towards the irradiation target 104. The irradiation target 104 includes an irradiation target material configured to emit gamma radiation 106 (i.e., prompt neutron capture gamma radiation) in response to incident thermal neutrons from the neutron generator 102. In some aspects, the irradiation target material has a high thermal neutron cross section. As used herein, a "high thermal neutron cross section" can mean a thermal neutron cross section greater that of hafnium-174. In other aspects, the irradiation target material can include gadolinium-157. In yet other aspects, the irradiation target material can have a thermal neutron cross section of about 257000 barns and/or greater than about 257000 barns.

The device 100 further includes an electron emitter 108. The electron emitter 108 includes an electron emitter material configured to emit delta radiation 110 in response to incident gamma radiation 106 emitted by the irradiation target 104. In some aspects, the electron emitter material can be high-Z material (e.g., a material having a high atomic number such as greater than 30, greater than 40, greater than 50, greater than 60, or greater than 70). In other aspects, the electron emitter material can include lead, tungsten, gold, platinum, or a combination thereof. The delta radiation 110 emitted by the electron emitter 108 may be delivered to a target region 114 within an object 112. In some aspects, the target region 114 is cancerous tissue (cancerous tissue 114) and the object 112 is a patient (patient 112). In this aspect, the delta radiation 110 is used to kill the cancerous tissue 114. In other aspects, the target region 114 and object 112 may be a target region of a semiconductor material (target region 114 of a semiconductor material 112). In this aspect, the delta radiation 108 can be used to increase the charge carrier concentration of the target region 114. Thus, in some aspects, device 100 may configured for cancer treatment. And in other aspects, device 100 may be configured to allow for the production of cheaper, deeper, and/or more uniform charge carrier density in gate devices compared to current electron beam methods.

In some aspects, device 100 can include shielding 116 that surrounds at least a portion of the device 100 and/or the components therein. For example, the shielding 116 may be configured to surround an end of an elongated portion of the neutron generator 102 and extend past the end of the elongated portion, surrounding the irradiation target 104. In some aspects, the shielding 116 may continue to extend past the end of the elongated portion of the neutron generator 102 up to a position of the electron emitter 108 and have an opening proximate to the target 114, as shown in FIG. 1. The shielding 116 includes a shielding material. In some aspects, the shielding material can include lead or another similar shielding material suitable for minimizing and/or preventing gamma radiation 106 from escaping the device 100. For example, the shielding 116 may be configured to minimize the amount of gamma radiation 106 that escapes the device 100 from the irradiation target 104 in a direction away from the electron emitter 108. In some aspects, the shielding material can include lead or another similar shielding material suitable for helping to containing the neutron flux field 118 within the device 100. For example, the shielding 116 may be configured to minimize the amount of neutron thermal neutrons (neutron flux field 118) that escape the device 100 from the neutron generator 102 in a direction away from the irradiation target 104. The shielding 116 may be configured to fit around a portion of the outer surface of the neutron generator 102 to minimize neutron 118 and/or gamma radiation 106 exposure to equipment that may be surrounding the device, for example, as needed to allow the use of the device in a hospital or office setting. The shielding 116, irradiation target 104, and/or electron emitter 108 may be configured to be used with traditional tubular-shaped electronic neutron generator designs.

In some aspects, device 100 can include a neutron moderator 120 that is positioned between the neutron generator 102 and the irradiation target 104. The neutron moderator 120 includes a neutron moderator material. The neutron moderator material and/or thickness thereof can be optimized the level of thermal neutron flux 118 at the irradiation target 104. This optimization may be performed using various software tools, such as Monte Carlo N-Particle Transport Code (MCNP). The neutron moderator may serve to help reduce the gamma radiation 106 being emitted from the device 100. The device 100 may include an access door and/or opening to allow for the placement of the neutron moderator 120 and/or other components of device 100.

Various aspects of the devices, systems, and methods disclosed herein can allow therapeutic doses of delta radiation to be delivered to a target area while controlling patient exposure to thermal neutron flux and gamma radiation. In one aspect, the use of an irradiation target including a material with a high thermal neutron cross section, such as gadolinium-157, allows for the generation of gamma radiation with higher energy at lower levels of incident neutron flux compared to materials with lower thermal neutron cross sections. For example, the thermal neutron cross section of gadolinium-157 is about 257000 barns. Conversely, the thermal neutron cross section of hafnium-174 is about 562 barns. As a result, the maximum energy of the prompt neutron capture gamma radiation emitted by gadolinium-157 is about 8 MeV whereas the maximum gamma radiation energy emitted by hafnium-174 is only about 3.3 MeV. Therefore, the delta radiation generated using an electron emitter material and gadolinium-157-emitted gamma radiation will be about twice as penetrating into patient tissue compared to delta radiation generated using the same electron emitter material and hafnium-174-emitted gamma radiation. Moreover, the use of an irradiation target material including gadolinium-157 requires a much smaller neutron flux to generate a therapeutic dose of delta radiation in a short time compared to hafnium-174-based materials. Thus, compared to previous methods, the devices, systems, and methods described above with respect to FIG. 1 can to deliver therapeutic doses of delta radiation with less exposure to potentially harmful neutron flux and gamma radiation.

Figure 2:
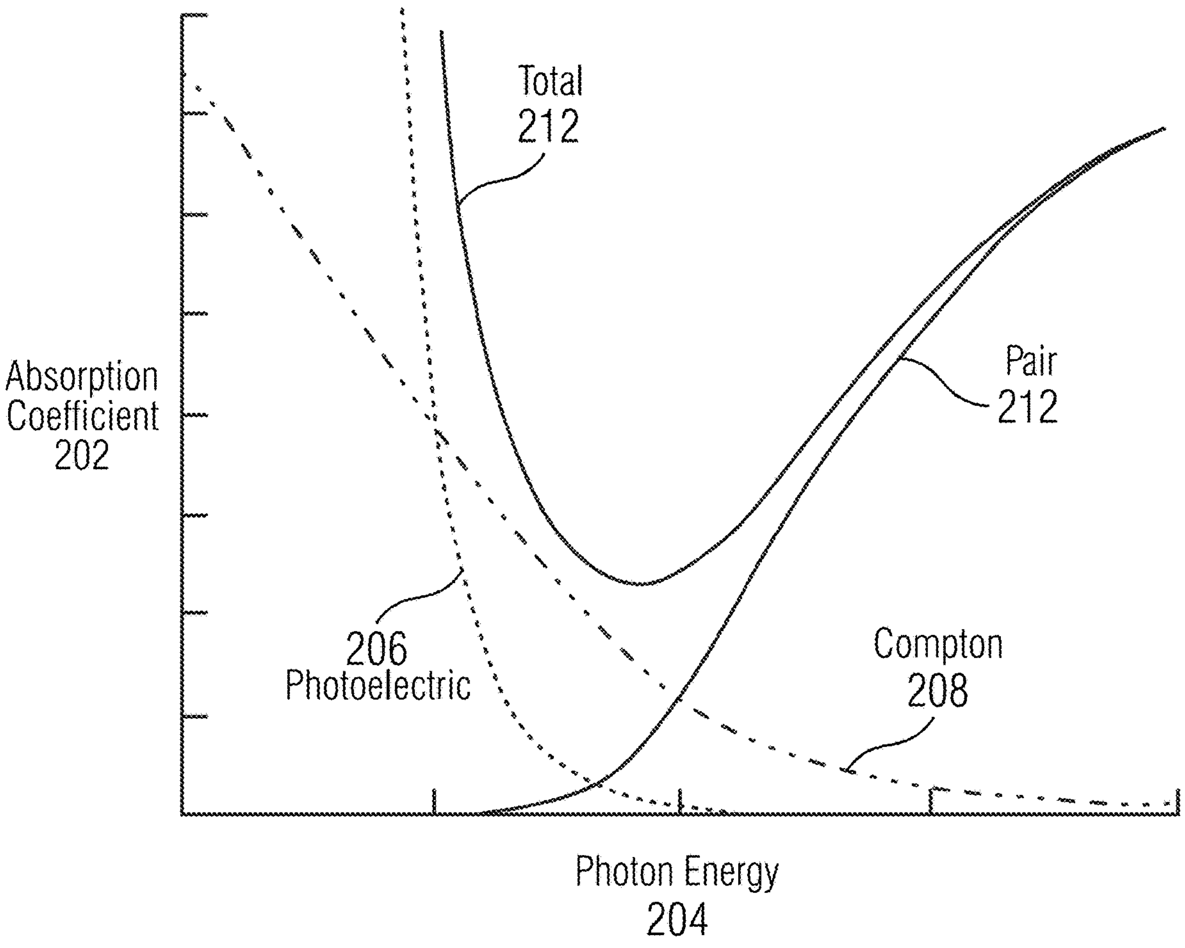
FIG. 2 is a line graph of the absorption coefficient of an exemplary material as a function of incident gamma radiation energy (i.e. photon energy), in accordance with at least one non-limiting aspect of the present disclosure.

In another aspect, the devices, systems, and methods described herein can take advantage of energy-dependent photoelectric and Compton scattering probabilities for various electron emitter materials. For example, FIG. 2 depicts a line graph of the absorption coefficient 202 (i.e. interaction probability) of an exemplary electron emitter material (i.e. lead) as a function of incident gamma radiation energy 204 (i.e. photon energy 204), in accordance with at least one non-limiting aspect of the present disclosure. As incident gamma radiation energy 204 decreases, probabilities for photoelectric 206 and Compton 208 scatting actually increase. Note that the total 212 probability curve is the combined probability of photoelectric 206, Compton 208, and pair 210 scattering. FIG. 2 is derived from Irving Kaplan, NUCLEAR PHYSICS, 408, Ch. 15 (2nd Ed.), which is incorporated by reference herein in its entirety.

Referring now to FIGS. 1 and 2, as photoelectric and Compton scattering can be the primary mechanisms for delta radiation 110 generation in device 100, the relationship shown in FIG. 2 indicates that gamma radiation 106 levels produced by device 100 may be limited such that the gamma radiation 106 is unable to escape the electron emitter 108 while still enabling the electron emitter 108 to emit therapeutic doses of delta radiation 110. In other aspects, gamma radiation 106 levels may be controlled such that, if gamma radiation 106 does escape the emitter 108, it substantially penetrates into the cancerous tissue 114. The intensity and energy of the gamma radiation 106 that would be experienced by the patient 112 using device 100 can be determined using a number of different commercially available software packages, such as MCNP. Additionally, the energy and intensity of delta radiation 110 that results from a given thickness of electron emitter 108 material, such as lead or Tungsten, and the incident neutron flux 118 interacting with the irradiator target 104 material may be similarly determined/optimized using such software. Accordingly, device 100 can allow for maximized delta radiation 110 intensity and energy while minimizing the gamma radiation 104 experienced by the patient 112.

Accordingly, various aspects of the present disclosure provide a novel treatment for skin cancer, lymphoma-related cancer, and/or other types of tumors and cancers. In some aspects, delta radiation can be directly applied to the site of cancer without exposing the patient to dangerous whole-body levels of gamma radiation and minimizing the time required to obtain a desired radiation dose. Moreover, aspects of the present disclosure may allow the medical community to more effectively treat skin cancer without the need to surgically remove sections of flesh from the patient.

Other aspects, the present disclosure provides novel devices, systems, and methods for the n-doping of semiconductor materials. For example, device 100 can be used to deliver an increased carrier concentration into a target region 114 of a semiconductor material 112 to control the electronic properties of a solid-state gate device. The device 100 can generate delta radiation 110 in the MeV range and have an intensity at the target region 114 that can be easily control by controlling the neutron flux 118 intensity, the distance between a surface of the electron emitter 108 and a surface of the semiconductor material 112, and/or the electron emitter 108 material. Thus, device 100 may allow for potentially cheaper, deeper, and more uniform n-doping of semiconductor materials compared to electron-beam generator approaches.

Exemplary capabilities of various devices, systems, and methods described herein are provided in the example below:

Example 1

Aspects of the devices and methods described herein were experimentally tested using the neutron beam laboratory at the Breazeale Nuclear Reactor (BNR) at Penn State University. A lead electron emitter with a thickness of about 5 cm and a surface area of 1 $cm^2$ was selected. It was determined that this electron emitter configuration can produce delta radiation with an average energy of about 0.4 MeV while delivering a gamma radiation dose to the patient at a rate of less than 20 mR/s. Assuming a neutron flux of $1 \times 10^8$ nv and a target $Gd_2O_3$ density of 7.07 gm/$cm^3$, the corresponding delta radiation dose rate is about 30 R/s. Current cancer treatment data suggest that a total therapeutic dose for skin cancer is about 4000 R. Therefore, the measurements obtained indicate the devices, systems, and methods described herein can be used to deliver a 4000 R dose of delta radiation in just over 2 minutes. During this time, the gamma dose to the patient would be less than 2.5 REM. This gamma dose may be considered to be therapeutic.

Various aspects of the devices, systems, and methods described herein are set out in the following clauses.

Clause 1: A device for delivering delta radiation using prompt neutron capture gamma radiation comprising: a neutron generator configured to generate a neutron flux field; an irradiation target configured to emit gamma radiation in response to exposure to the neutron flux field; and an electron emitter configured to emit delta radiation in response to exposure to the gamma radiation; wherein the irradiation target and the electron emitter are configured to be positioned between the neutron generator and a surface of an object to deliver the delta radiation to a target region within the object; and wherein the irradiation target comprises an irradiation target material having a high thermal neutron cross section.

Clause 2: The device of Clause 1, wherein the irradiation target material comprises gadolinium-157.

Clause 3: The device of any of Clauses 1-2, wherein the electron emitter comprises an electron emitter material, the electron emitter material comprising a high-Z material.

Clause 4: The device of any of Clauses 1-3, wherein the electron emitter material comprises tungsten, lead, or a combination thereof.

Clause 5: The device of any of Clauses 1-4, further comprising radiation shielding configured to minimize an amount of the gamma radiation that escapes the device from the irradiation target in a direction away from the electron emitter.

Clause 6: The device of any of Clauses 1-5, further comprising radiation shielding configured to maximize the containment of the neutron flux field within the device.

Clause 7: The device of any of Clauses 1-6, further comprising a neutron moderator positioned between an end of the neutron generator and the irradiation target, wherein the neutron moderator is configured to optimize the exposure of the irradiation target to the neutron flux field.

Clause 8: The device of any of Clauses 1-7, wherein the object is a patient and the target region is cancerous tissue.

Clause 9: The device of any of Clauses 1-8, wherein the object is a semiconductor material.

Clause 10: A method for delivering delta radiation using prompt neutron capture gamma radiation comprising: generating, by a neutron generator, a neutron flux field; emitting, by an irradiation target comprising an irradiation target material having a high thermal neutron cross section, gamma radiation in response to exposure to the neutron flux field: emitting, by an electron emitter, delta radiation in response to exposure to the gamma radiation; positioning the irradiation target and the electron emitter between the neutron generator and a surface of an object; and delivering the delta radiation to a target region within the object.

Clause 11: The method of Clause 11, wherein the irradiation target material comprises gadolinium-157.

Clause 12: The method of any of Clauses 10-11: wherein the electron emitter comprises an electron emitter material, the electron emitter material comprising a high-Z material.

Clause 13: The method of any of Clauses 10-12: wherein the electron emitter material comprises tungsten, lead, or a combination thereof.

Clause 14: The method of any of Clauses 10-13: further comprising minimizing, by shielding, an amount of the gamma radiation that escapes the device from the irradiation target in a direction away from the electron emitter.

Clause 15: The method of any of Clauses 10-14: further comprising, maximizing, by shielding, the containment of the neutron flux field within the device.

Clause 16: The method of any of Clauses 10-15: further comprising optimizing, by a neutron moderator, the exposure of the irradiation target to the neutron flux field.

Clause 17: The method of any of Clauses 10-16: wherein delivering the delta radiation to a target region within the object comprises delivering the delta radiation to cancerous tissue of a patient.

Clause 18: The method of any of Clauses 10-17: further comprising, receiving, by the cancerous tissue, a dose of the delta radiation of no less than 4000 R in 2 minutes.

Clause 19: The method of any of Clauses 10-18: further comprising, receiving, by the patient, a dose of the gamma radiation less than 2.5 REM.

Clause 20: The method of any of Clauses 10-19: further comprising, containing, by the electron emitter, the gamma radiation exposed thereto.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The term "substantially", "about", or "approximately" as used in the present disclosure, unless otherwise specified, means an acceptable error for a particular value as determined by one of ordinary skill in the art, which depends in part on how the value is measured or determined. In certain embodiments, the term "substantially", "about", or "approximately" means within 1, 2, 3, or 4 standard deviations. In certain embodiments, the term "substantially", "about", or "approximately" means within 50%, 20%, 15%, 10%, 9%, 8%, 7%, 6%, 5%, 4%, 3%, 2%, 1%, 0.5%, or 0.05% of a given value or range.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A device for delivering delta radiation to a target region of an object using prompt neutron capture gamma radiation, the device comprising:

a neutron generator configured to generate a neutron flux field from an end of the neutron generator;

an irradiation target configured to emit gamma radiation in response to exposure to the neutron flux field, the irradiation target positioned proximate the end of the neutron generator;

an electron emitter configured to emit delta radiation in response to exposure to the gamma radiation, the electron emitter positioned proximate the irradiation target, wherein the irradiation target is intermediate the electron emitter and the end of the neutron generator; and radiation shielding surrounding at least a portion of the device, wherein the radiation shielding surrounds the end of the neutron generator and extends past the end of the neutron generator to surround the irradiation target, wherein the radiation shielding is configured to prevent at least some of the gamma radiation from exiting the device;

wherein the irradiation target comprises an irradiation target material having a high thermal neutron cross section.

2. The device of claim 1, wherein the irradiation target material comprises gadolinium-157.

3. The device of claim 1, wherein the electron emitter comprises an electron emitter material, the electron emitter material comprising a high-Z material.

4. The device of claim 3, wherein the electron emitter material comprises tungsten, or lead, or a combination thereof.

5. The device of claim 1, wherein the at least a portion of the device surrounded by the radiation shielding further comprises the electron emitter, and wherein the radiation shielding comprises an opening proximate the electron emitter.

6. The device of claim 1, wherein the radiation shielding is configured to prevent at least some of the neutron flux field from exiting the device.

7. The device of claim 1, further comprising a neutron moderator positioned between the end of the neutron generator and the irradiation target, wherein the neutron moderator is configured to optimize the exposure of the irradiation target to the neutron flux field.

8. The device of claim 1, wherein the object is a patient and the target region is cancerous tissue.

9. The device of claim 1, wherein the object is a semiconductor material.

10. A method for operating a device to deliver delta radiation using prompt neutron capture gamma radiation, wherein the device comprises a neutron generator, an electron emitter positioned proximate an end of the neutron generator, an irradiation target positioned intermediate the electron emitter and the end of the neutron generator, and radiation the device, wherein the radiation shielding surrounds the end of the neutron generator and extends past the end of the neutron generator to surround the irradiation target, wherein the method comprises:

generating, by the neutron generator, a neutron flux field from the end of the neutron generator;

emitting, by the irradiation target comprising an irradiation target material having a high thermal neutron cross section, gamma radiation in response to exposure to the neutron flux field; and emitting, by the electron emitter, delta radiation in response to exposure to the gamma radiation.

11. The method of claim 10, wherein the irradiation target material comprises gadolinium-157.

12. The method of claim 11, wherein the electron emitter comprises an electron emitter material, the electron emitter material comprising a high-Z material.

13. The method of claim 12, wherein the electron emitter material comprises tungsten, or lead, or a combination thereof.

14. The method of claim 10, further comprising minimizing, by the radiation shielding, the gamma radiation that escapes the device from the irradiation target in a direction away from the electron emitter.

15. The method of claim 10, further comprising, preventing, by the radiation shielding, at least some of the neutron flux field from exiting the device.

16. The method of claim 10, wherein the device further comprises a neutron moderator intermediate the irradiation target and the end of the neutron generator, the method further comprising optimizing, by a neutron moderator, the exposure of the irradiation target to the neutron flux field.

17. The method of claim 10, further comprising delivering the delta radiation to a target region within an object.

18. The method of claim 17, wherein delivering the delta radiation to the target region comprises delivering a dose of the delta radiation to the target region of no less than 4000 R in 2 minutes.

19. The method of claim 18, wherein the target region receives a dose of the gamma radiation less than 2.5 REM.

20. The method of claim 10, further comprising, containing, by the electron emitter, the gamma radiation within the device.

* * * * *